US00PP22240P2

(12) United States Plant Patent
Hartman

(10) Patent No.: US PP22,240 P2
(45) Date of Patent: Nov. 8, 2011

(54) ***CALADIUM* PLANT NAMED 'WHITE DYNASTY'**

(50) Latin Name: *Caladium×hortulanum*
Varietal Denomination: White Dynasty

(76) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 12/802,579

(22) Filed: Jun. 9, 2010

(51) Int. Cl.
*A01H 5/00* (2006.01)

(52) U.S. Cl. ..... Plt./373
(58) Field of Classification Search ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'White Dynasty', characterized by its upright and mounding plant habit; intermediate to tall plant size; uniform potted plant habit with or without de-eyeing tubers; vigorous and dense growth habit; fast growth rate; and lance-type leaves that are white and greyed green with few random red purple-colored spots, dark green-colored margins and greyed green-colored venation.

4 Drawing Sheets

Botanical designation: *Caladium×hortulanum.*
Cultivar denomination: 'WHITE DYNASTY'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'White Dynasty'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2003, in Lake Placid, Fla. of *Caladium×hortulanum* 'White Wing', not patented, as the female, or seed, parent with *Caladium×hortulanum* 'Aaron', not patented, as the male, or pollen, parent. The new *Caladium* plant was discovered and selected by the Inventor as a single plant within the progeny of the stated cross-pollination in a controlled outdoor nursery environment in Lake Placid, Fla. on Aug. 15, 2004.

Asexual reproduction of the new *Caladium* plant by tuber divisions in a controlled outdoor nursery environment in Lake Placid, Fla. since Apr. 15, 2005 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'White Dynasty' . These characteristics in combination distinguish 'White Dynasty' as a new and distinct *Caladium* plant:

1. Upright and mounding plant habit; intermediate to tall plant size.
2. Uniform potted plant habit with or without de-eyeing tubers.
3. Vigorous and dense growth habit.
4. Fast growth rate.
5. Lance-type leaves that are white and greyed green with few random red purple-colored spots, dark green-colored margins and greyed green-colored venation.

Plants of the new *Caladium* differ primarily from plants of the female parent, 'White Wing', in the following characteristics:

1. Plants of the new *Caladium* grow faster than plants of 'White Wing'.
2. Plants of the new *Caladium* have broader leaves than plants of 'White Wing'.
3. Plants of the new *Caladium* and 'White Wing' differ in leaf coloration as plants of 'White Wing' have white and green-colored leaves with mottled green-colored margins and pink to white-colored venation.

Plants of the new *Caladium* differ primarily from plants of the male parent, 'Aaron', in the following characteristics:

1. Plants of the new *Caladium* are shorter and more mounding than plants of 'Aaron'.
2. Plants of the new *Caladium* have broader leaves than plants of 'Aaron'.
3. Plants of the new *Caladium* and 'Aaron' differ in leaf coloration as plants of 'Aaron' have white and green-colored leaves with white-colored venation.

Plants of the new *Caladium* can be compared to plants of 'Jackie Suthers', not patented. In side-by-side comparisons conducted in Lake Placid, Fla., plants of the new *Caladium* differed primarily from plants of 'Jackie Suthers' in the following characteristics:

1. Plants of the new *Caladium* grew slower than plants of 'Jackie Suthers'.
2. Plants of the new *Caladium* were taller and more upright than plants of 'Jackie Suthers'.
3. Plants of the new *Caladium* and 'Jackie Suthers' differed in leaf coloration as plants of 'Jackie Suthers' had white and green-colored leaves with green-colored margins and white-colored venation.

Plants of the new *Caladium* can also be compared to plants of 'Grey Ghost', not patented. In side-by-side comparisons conducted in Lake Placid, Fla., plants of the new *Caladium* differed primarily from plants of 'Grey Ghost' in the following characteristics:

1. Plants of the new *Caladium* were shorter and more mounding than plants of 'Grey Ghost'.
2. Plants of the new *Caladium* had ovate-shaped leaves whereas plants of 'Grey Ghost' had cordate-shaped leaves.
3. Plants of the new *Caladium* and 'Grey Ghost' differed in leaf coloration as plants of 'Grey Ghost' had white and green-colored leaves with white-colored venation.

BRIEF DESCRIPTION OF THE PHOTOGRAPHS

The accompanying photographs illustrate the overall appearance of the new *Caladium* plant. These photographs show the colors as true as it is reasonably possible to obtain in colored reproductions of this type. Colors in the photographs may differ slightly from the color values cited in the detailed botanical description which accurately describe the colors of the new *Caladium* plant.

The photograph at the top of first sheet is a side perspective view of a typical plant of 'White Dynasty' grown from non de-eyed tubers in a container in a shadehouse.

The photograph at the bottom of first sheet is a side perspective view of a typical plant of 'White Dynasty' grown from de-eyed tubers in a container in a shadehouse.

The photograph on the second sheet is a close-up view of a typical inflorescence of 'White Dynasty'.

The photograph at the top of the third sheet is a top perspective view of typical plants of 'White Dynasty' grown in an outdoor nursery.

The photograph at the bottom of the third sheet is a close-up view of typical freshly-dug tubers and roots of 'White Dynasty'.

The photograph at the top of the fourth sheet is a side perspective view of typical potted plants of the female parent, 'White Wing' (left), 'White Dynasty' (center) and the male parent, 'Aaron' (right).

The photograph at the bottom of the fourth sheet is a side perspective view of typical potted plants of 'Jackie Suthers' (left), 'White Dynasty' (center) and 'Grey Ghost' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown in ground beds in an outdoor nursery in Zolfo Springs, Fla. during the late summer and autumn. All plants were grown under conditions and practices which approximate those generally used in commercial *Caladium* production. During the production of the plants, day temperatures ranged from about 20° C. to 35° C., night temperatures ranged from about 10° C. to 26° C. and light levels were about 8,000 foot-candles (shadehouse) or 10,000 to 12,000 foot-candles (outdoor nursery). Plants had been growing in the shadehouse for nine weeks from planting tubers when the photographs and the detailed description were taken. Plants had been growing in the outdoor nursery for six months from planting tuber divisions when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'White Dynasty'.

Parentage:

*Female, or seed, parent.*—*Caladium×hortulanum* 'White Wing', not patented.

*Male, or pollen, parent.*—*Caladium×hortulanum* 'Aaron', not patented.

Propagation:

*Type.*—By tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate in shape. Height: About 3.1 cm. Diameter: About 3.6 cm. Texture: Thick and starchy; somewhat brittle. Color: Epidermis, between 165B and N170C to N170D, just below surface, close to 36A; interior, close to 155B to 4D. Root description: Dense, thick, fleshy contractile roots with few lateral branches; color, close to 155C.

Plant description:

*Plant type.*—Herbaceous perennial; suitable as a potted plant in containers 15-cm to 25-cm and also suitable as a landscape plant. Plant and growth habit: Upright and mounding plant habit; intermediate to tall plant size; inverted triangle; vigorous and dense growth habit; rapid growth rate; petioles and leaves arise from one or more growing points on tubers; petioles mostly upright and leaning outwardly with development.

*Plant height, from soil level to top of leaf plane, shadehouse-grown plants.*—About 21 cm to 25 cm.

*Plant height, from soil level to top of inflorescences, shadehouse-grown plants.*—About 34.5 cm.

*Plant diameter or spread, shadehouse-grown plants.*—About 37 cm to 43 cm.

*Number of clumps per plant, shadehouse-grown plants.*—About 15 from tubers.

*Cataphylls, shadehouse-grown plants.*—Length: About 5 cm to 8 cm. Width: About 1.5 cm to 2.1 cm. Shape: Triangular, wedge-shaped. Apex: Acuminate. Base: Sheathing the stem. Color, inner and outer surfaces: Close to N155A streaked/tessellated with close to 147A to 147B; with development, color becoming closer to N199B stained with close to 187B.

Foliage description:

*Length, shadehouse-grown plants.*—About 15 cm to 18.5 cm.

*Width, shadehouse-grown plants* (*flattened*).—About 8.4 cm to 13 cm.

*Shape.*—Ovate.

*Apex.*—Acuminate.

*Base.*—Sagittate to cordate.

*Margin.*—Entire with broad undulations.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Areas of close to 155C, close to 194B and close to 194C; occasional random spots towards the base, close to 59B. Margins: Towards the margins, close to 147A and close to 194B; margins, close to 147A and close to N189A; basal notch, close to 59A. Venation: Midrib, close to 194C to 194D; primary veins, close to 194B. Developing leaves, lower surface: Center: Close to 155C. Margins: Towards the margins, close to 147B to 147C; margin, close to 147B tinged with close to N138C; basal notch, close to 59A. Venation: Midrib, close to 147C tinged with close to 160D; primary veins, close to 147C, streaks, close to 146B. Fully expanded leaves, upper surface: Center: Areas of close to 155C and close to 194C; occasional random spots mostly towards the base, close to 155C faintly tinged with close to 59B and close to 59B. Margins: Towards the margins, close to 147A, close to 146A and close to 194B; margins, close to 147A and close to N189A; basal notch, close to 59A. Venation: Midrib, close to 194B; primary veins, close to 194B. Fully expanded leaves, lower surface: Center: Areas close to 155C and close to 147C. Margins: Towards the margins, close to 147B to 147C, close to 146B to 146C and close to 155C; margin, close to 147B tinged with close to N138C; basal notch, close to 59A. Venation: Midrib, close to 147C tinged with close to 160D; primary veins, close to 147C, streaks, close to 146B.

*Petiole.*—Aspect: Mostly erect, outwardly leaning and arching with development; flexible. Length, shadehouse-grown plants: About 16 to 18 cm. Diameter, distal, shadehouse-grown plants: About 3.5 mm. Diameter, proximal, shadehouse-grown plants: About 8 mm to 13 mm. Color, shadehouse-grown plants: Close to 147B tinged with close to 199D and streaked/tessellated with close to 147A and close to 187B. Wing length, shadehouse-grown plants: About 7 cm to 9 cm. Wing diameter, shadehouse-grown plants: About 7.5 mm to 9 mm. Wing color, shadehouse-grown plants, outer and inner surfaces: Close to N155A streaked/tessellated with close to 147A to 147B.

Inflorescences description: Inflorescences observed on shadehouse-grown plants.

*Inflorescence arrangement.*—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop between female and male flower zones; near this area, the spathe constricts and surrounds and encloses the female flowers; spathe open and cupped around male flowers.

*Fragrance.*—None detected.

*Natural flowering season/longevity.*—Plants of the new *Caladium* typically flower during the spring or early summer in central Florida; flowers develop about ten weeks after growth commences; inflorescences last about three days before fading; inflorescences persistent.

*Spathe.*—Length: About 12.3 cm; open length, about 8.9 cm and closed length, about 3.4 cm. Width, distal: About 3 cm. Width, proximal: About 2.5 cm. Width, at constriction: About 1.7 cm. Shape: Ovate. Apex: Acute to acuminate. Base: Tapering to the peduncle. Margin: Entire. Texture, upper and lower surfaces: Smooth, glabrous. Color: Front surface: Upper two-thirds: Close to 155C tinged with close to 157A; with development, color becoming closer to 199C to 199D. Lower one-third: Close to 147C to 147D; with development, color becoming closer to 147B streaked/ mottled with close to 146B to 146C. Rear surface: Upper two-thirds: Close to 155A tinged with close to 145C. Lower one-third: Close to 147B streaked with close to 146B to 146C. Spadix: Length: About 7.1 cm. Length, male flower zone: About 4.3 cm. Length, female flower zone: About 1.8 cm. Length, sterile flower zone: About 1 cm. Diameter, male flower zone: About 1.1 cm. Diameter, female flower zone: About 1 cm. Diameter, sterile flower zone: About 8 mm. Shape: Columnar. Apex: Obtuse. Base: Obtuse. Aspect: Upright. Color, mature, male zone: Close to 158D tinged with close to 150D. Color, mature, sterile zone: Close to 158D tinged with close to 150D. Color, mature, female zone: Close to 20D. Male flowers: Quantity per spadix: About 180. Shape: Obovate. Height: About 3 mm. Diameter: About 3 mm. Anthers: None observed. Female flowers: Quantity per spadix: About 140. Shape: Obovate. Height: About 3 mm. Diameter: About 2 mm. Stigma color: Close to 20D. Ovary color: Close to 155D. Scape: Length: About 22.2 cm. Diameter: About 6 mm. Strength: Sturdy; flexible. Aspect: Erect. Texture: Smooth, glabrous; glaucous. Color: Close to 147A tinged with close to 146A with fine and faint striations/tessellations close to 147A and close to 187B; just below spathe, close to 148B. Seed and fruit: Seed and fruit development have not been observed on plants of the new *Caladium*.

Disease/pest resistance: Plants of the new *Caladium* have been observed to be relatively tolerant to *Pythium* root rot and *Xanthomonas* leaf blight. Plants of the new *Caladium* have not been observed to be resistant to pests or other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed::

1. A new and distinct *Caladium* plant named 'White Dynasty' as illustrated and described.

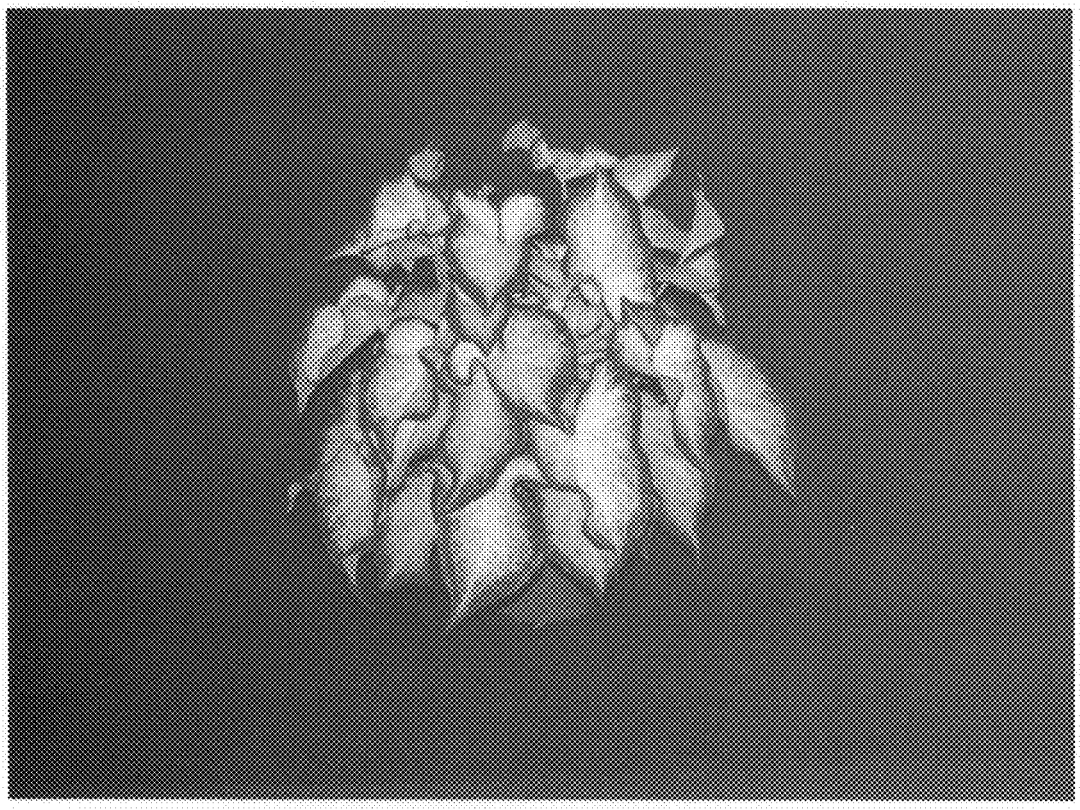
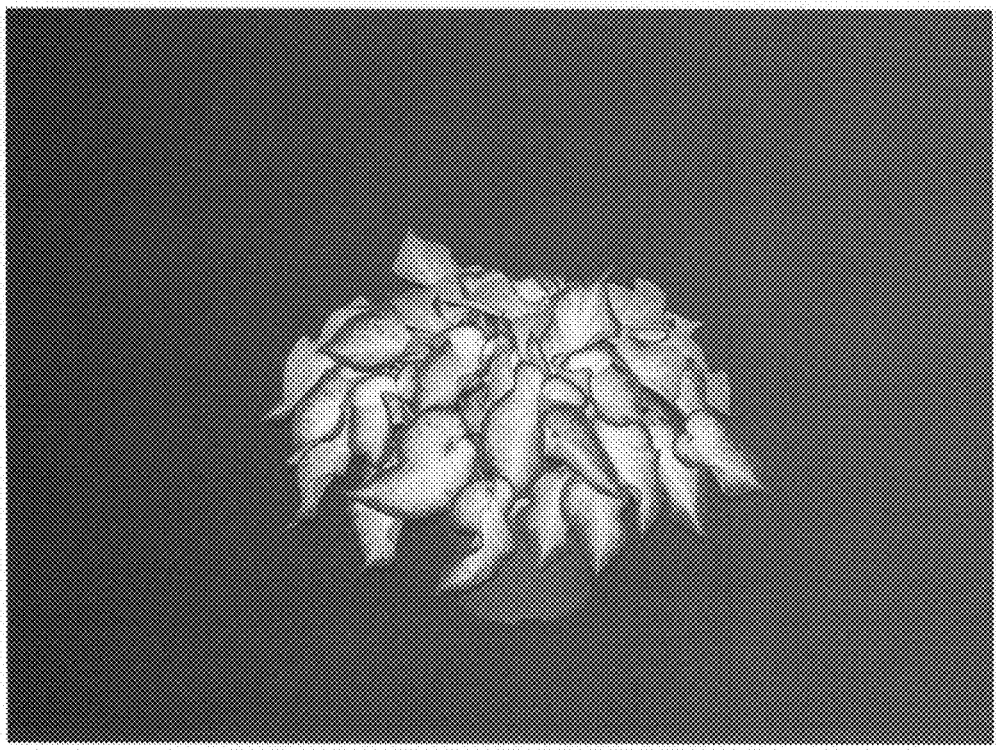

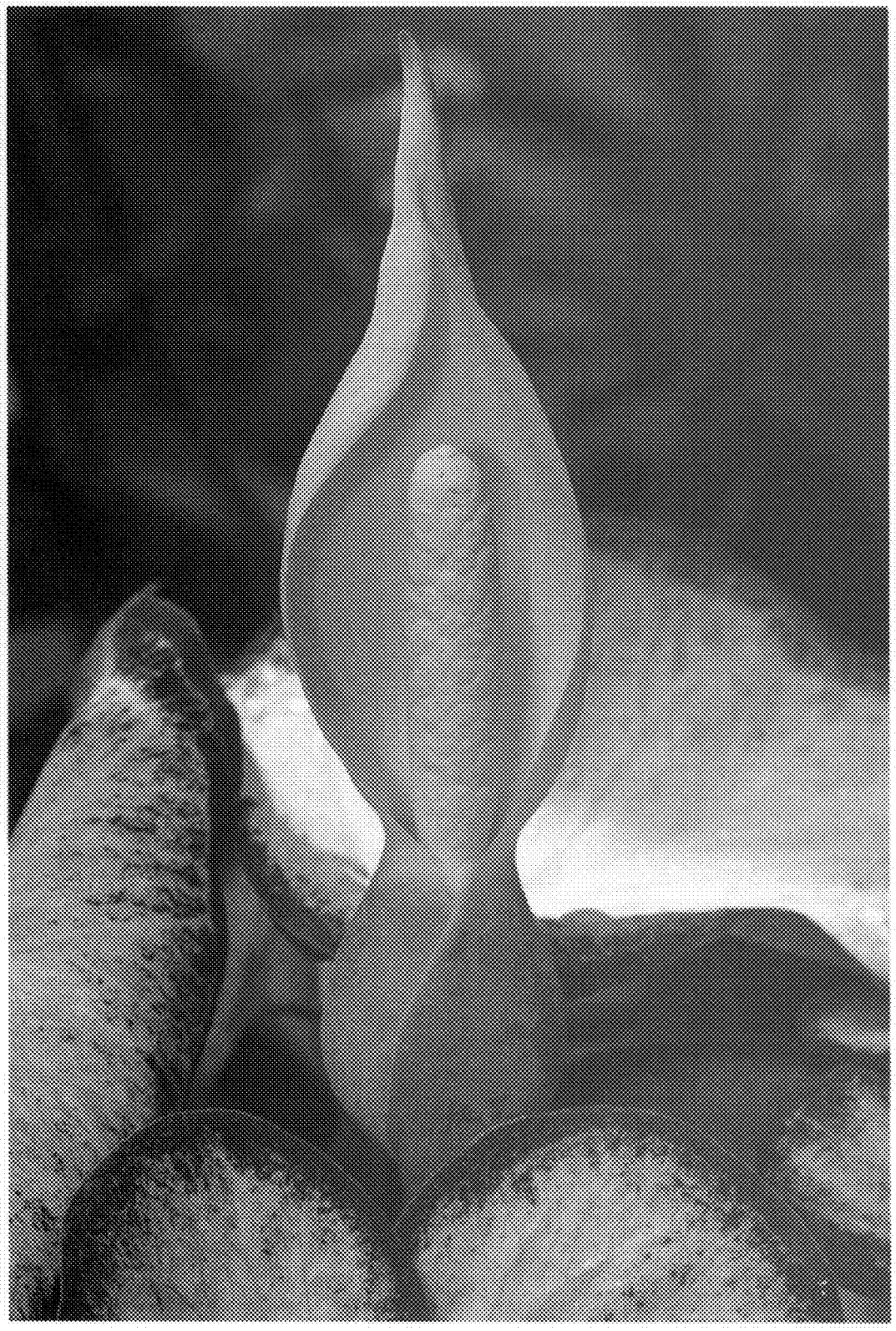

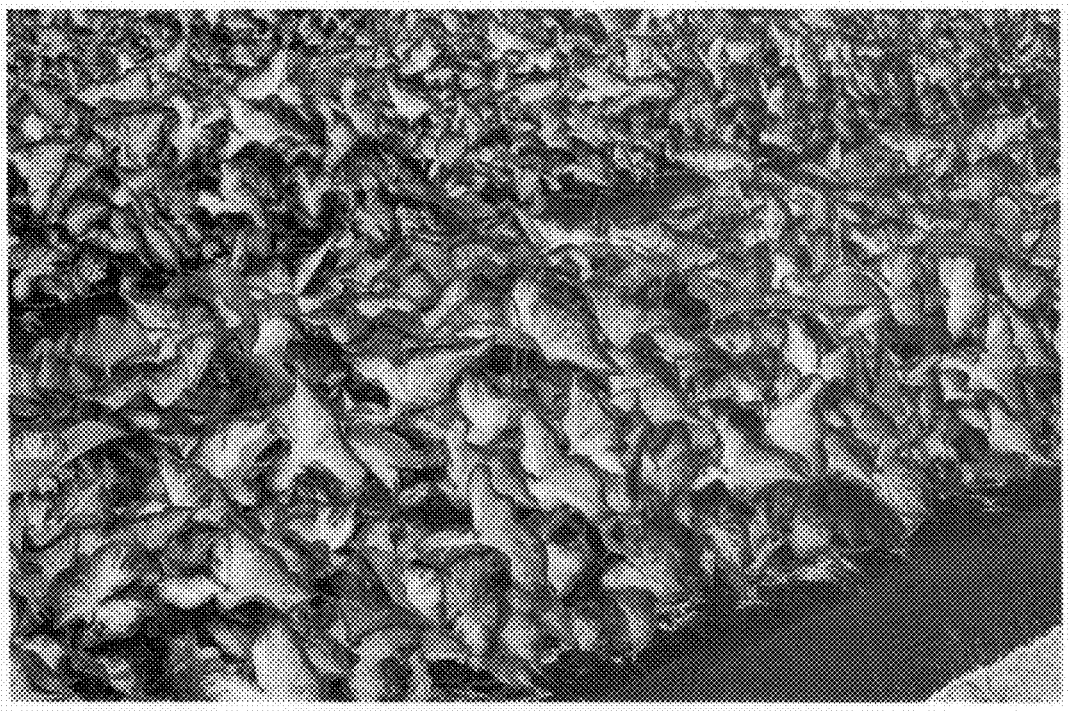
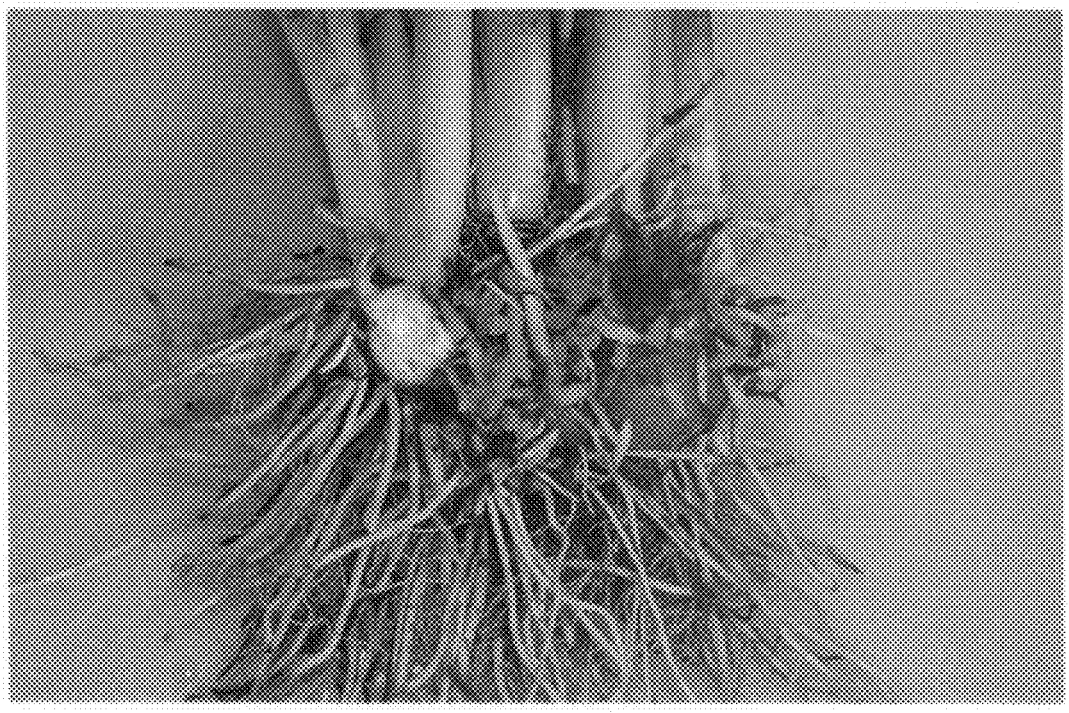

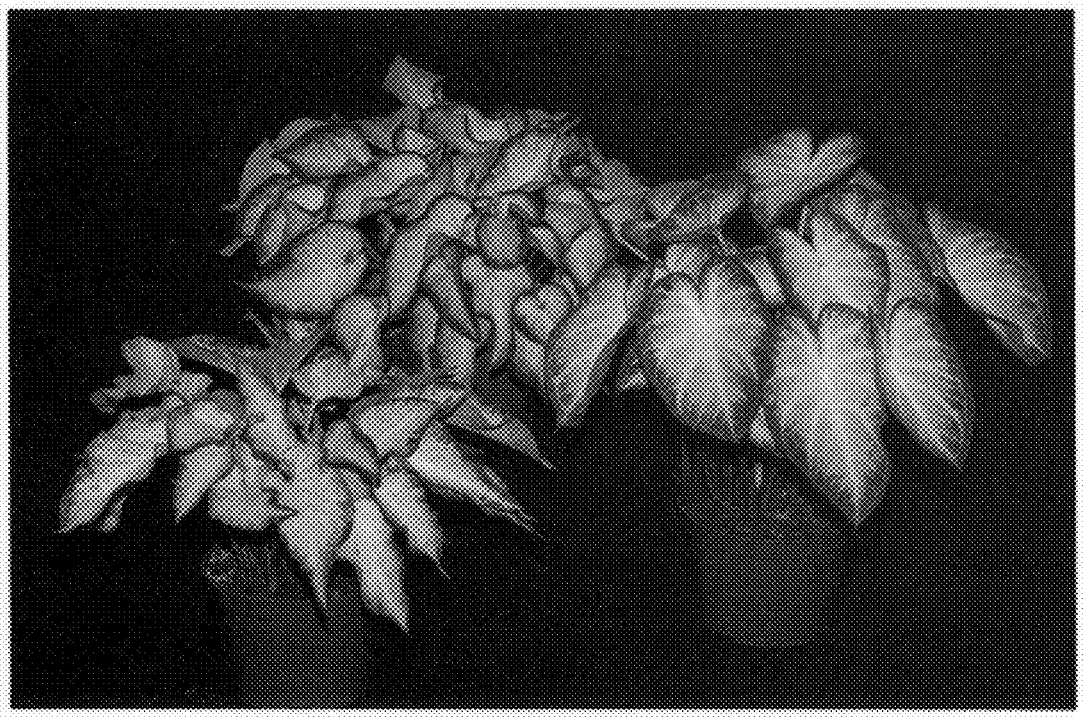
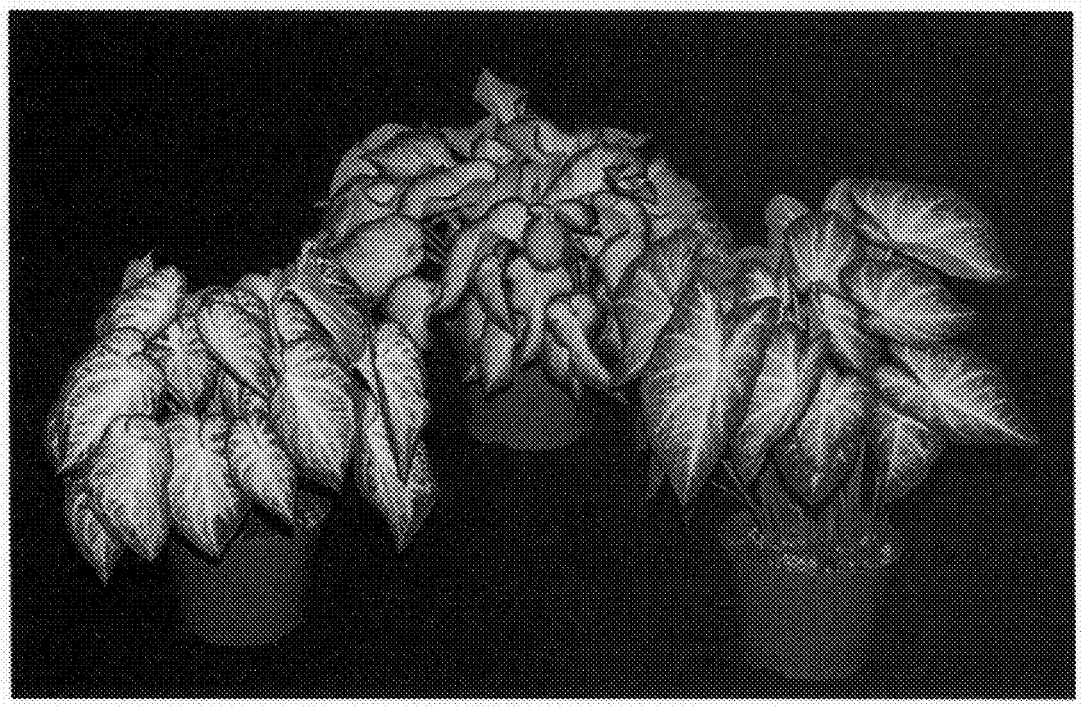

* * * * *